United States Patent [19]

Toronto et al.

[11] Patent Number: 5,217,431
[45] Date of Patent: Jun. 8, 1993

[54] ORTHOPEDIC ANKLE BRACE

[75] Inventors: Russell A. Toronto, Salt Lake City, Utah; Charles A. Bastyr, San Diego, Calif.

[73] Assignee: Smith & Nephew Donjoy, Inc., Carlsbad, Calif.

[21] Appl. No.: 839,468

[22] Filed: Feb. 20, 1992

[51] Int. Cl.⁵ .............................................. A61F 5/00
[52] U.S. Cl. ........................................ 602/27; 602/65
[58] Field of Search ................................ 602/27–29, 602/5, 23, 65

[56] References Cited

U.S. PATENT DOCUMENTS

| | | | |
|---|---|---|---|
| 3,073,305 | 1/1963 | Biggs, Jr. et al. | 602/65 |
| 3,674,023 | 2/1972 | Mann | 602/65 |
| 4,313,433 | 2/1982 | Cramer | 602/27 |
| 4,367,733 | 1/1983 | Stromgun | 602/65 |
| 4,495,942 | 1/1985 | Palumbo . | |
| 4,590,932 | 5/1986 | Wilkerson . | |
| 4,630,600 | 12/1986 | Spencer et al. | 602/27 |
| 4,702,234 | 10/1987 | Huntjens | 602/65 X |
| 4,729,370 | 3/1988 | Kallassy . | |
| 4,753,229 | 6/1988 | Sutherland | 602/27 |
| 4,844,058 | 7/1989 | Vogelbach | 602/27 |
| 4,962,768 | 10/1990 | Stromgren et al. | 602/27 |
| 5,016,623 | 5/1991 | Krahenbuhl | 602/27 |
| 5,067,486 | 11/1991 | Hely | 602/27 |
| 5,090,404 | 2/1992 | Kallassy | 602/23 X |
| 5,099,860 | 3/1992 | Anrein | 602/27 |

FOREIGN PATENT DOCUMENTS

WO89/10731 11/1989 PCT Int'l Appl. .

Primary Examiner—Richard J. Apley
Assistant Examiner—Linda C. M. Dvorak
Attorney, Agent, or Firm—Rodney F. Brown

[57] ABSTRACT

An orthopedic ankle brace is provided having a pliant boot that surrounds the ankle joint, as well as the foot and lower leg in the region thereof. The boot may incorporate means of applying compression to the ankle joint. Attached to the boot are a pair of adjustable tension straps vertically disposed about the ankle joint for restricting the mobility thereof. Integral with the boot are pair of stiffening members positioned about the ankle joint to cooperate with the tension straps in the performance of their mobility restricting function Further provided integral with the boot are retention members that isolate the malleoli from the stiffening members for the comfort of the wearer. Finally, one or more retention straps are provided to maintain the stability of the brace.

18 Claims, 6 Drawing Sheets

ORTHOPEDIC ANKLE BRACE

FIELD OF THE INVENTION

The present invention relates generally to orthopedic treatment devices, particularly to an ankle brace, and more particularly to a pliant ankle brace providing both compression and stability to the entire ankle joint region.

BACKGROUND OF THE INVENTION

In the treatment of soft tissue or skeletal injuries to the ankle joint, it is preferable to stabilize the ankle joint as well as portions of the foot and leg in the region of the ankle joint. At the outset, when the injury is in the acute rehabilitation phase, stabilization of the ankle joint generally comprises compression and significant mobility restriction thereof to reduce swelling and facilitate healing. As treatment progresses and the injury enters the return to activity phase, stabilization of the ankle joint generally requires lesser, yet still somewhat significant, mobility restriction thereof.

In the past, stabilization of the injury during the acute rehabilitation phase has required casting of the ankle joint, thereby immobilizing it. Removable ankle braces became available which could subsequently be used to stabilize the injury during the return to activity phase. Once the ankle joint was fully rehabilitated, a removable ankle brace could also be worn as a prophylaxis on the healthy ankle joint to minimize the risk of re-injury during activity. More recently, removable ankle braces have been developed which can even be employed during the acute rehabilitation phase of the injury in the place of a cast.

It is apparent that each phase of the injury has different performance requirements for the ankle brace. While presently-available ankle braces have specific utility for a given injury phase, no one ankle brace is sufficiently versatile to be useful throughout treatment of the ankle joint injury and thereafter when the ankle joint is fully rehabilitated. Thus, known ankle braces are found to exhibit at least one of the following deficiencies lack of compression, incomplete protection of the injury, discomfort when worn with a shoe, and cumbersome when engaging in activity. As such, a need exists for an ankle brace that overcomes these deficiencies and provides effective stabilization of the ankle joint during various stages of treatment or activity.

It is an object of the present invention to provide an orthopedic ankle brace that is sufficiently versatile to have utility in the acute and return to activity phases of an injury, as well as having utility as a prophylaxis for a healthy ankle joint. It is also an object of the present invention to provide an ankle brace that is capable of providing compression to the ankle joint while adequately restricting mobility of the ankle joint during the acute phase of the injury. It is further an object of the present invention to provide an ankle brace that is capable of being comfortably worn under a shoe and which is not cumbersome to wear during activity.

SUMMARY OF THE INVENTION

The present invention is an orthopedic ankle brace for stabilizing the ankle joint as well as the foot and lower leg in the region of the ankle joint. The brace has specific utility for the treatment of ankle joint injuries, including both bone and soft tissue injuries. The brace is particularly effective during the acute rehabilitation phase immediately following the injury, or thereafter during the return to activity phase of the injury. The brace also has utility as a prophylaxis for healthy ankle joints to prevent new injuries or the reoccurrence of old injuries during activity. Accordingly, the brace is described hereafter in the context of its useful environment and in reference to those parts of the body with which the brace aligns and interacts.

The brace of the present invention comprises a pliant boot that wraps around and conforms to the contours of the ankle joint, thereby substantially enclosing the joint. When in place about the ankle joint, the boot has a proximal segment extending vertically and encircling the lower leg immediately above the ankle joint in the region of the distal tibia. The boot also has a distal segment extending horizontally and encircling the foot immediately below the ankle joint in the region of the plantar vault. The two segments intersect at the ankle joint, to provide a unitary boot.

The boot has a proximal opening through which the lower leg extends into the boot and a distal opening through which the distal end of the foot extends from the boot. A posterior opening is also provided at the base of the boot through which the tuberosity of the calcaneus extends, thereby serving as a heel lock for the brace when it is in position about the ankle joint. In a first embodiment, the brace further has an anterior opening extending the length of the boot which enables application of the brace onto the ankle joint and adjacent leg and foot.

A pair of flaps are provided across the anterior opening of the first embodiment, extending from one side of the boot to the opposite side thereof, and being releasably fastenable by means of releasable fasteners on each flap. The first flap is positioned on the proximal segment of the boot and the second flap is positioned below it on the distal segment. Unfastening of the flaps enables ready application of the boot to the ankle joint or ready removal therefrom, while fastening of the flaps secures the boot thereto. The releasable fasteners further enable adjustable tension of the fastened flaps, thereby enabling compression adjustment of the boot around the ankle joint.

Integral with each side of the proximal segment is a stiffening member which is formed from a more rigid material than that of the boot. The stiffening member is an elongated element extending vertically along the length of the proximal segment and terminating above the malleolus of the ankle joint. The stiffening member imparts a higher degree of stiffness to the side of the proximal segment than the pliant boot material.

Further provided integral with each side of the proximal segment is a retention member that is of intermediate rigidity relative to the pliant boot and stiffener members. The retention member is positioned immediately distal each stiffening member on the proximal segment of the boot at its intersection with the distal segment. In this position, the retaining member fits around the malleolus in abutment therewith, forming a malleolus pocket to isolate the malleolus from the stiffening member for the comfort of the wearer.

Affixed to the boot are a pair of tension straps which enhance the stabilizing effect of the brace on the ankle joint when the straps are in place. The first tension strap is anterior relative to the second tension strap and permits variable tension control of forefoot inversion and, to a lesser degree, variable tension control of internal rotation. This first, or anterior, tension strap has two ends and attachment means provided at each end for attaching the ends to the boot. More specifically, one end of the anterior tension strap is attached to the distal segment on one side of the boot and the other end of the anterior tension strap is attached to the proximal segment on the opposite side of the boot.

In the above-described configuration, the anterior tension strap extends from its point of attachment on the distal segment of the boot around the bottom of the distal segment abutting the plantar vault to the point of attachment at the proximal segment on the opposite side of the boot. Guides may be provided integral with the boot to maintain the position of the anterior tension strap relative to the boot. Furthermore, at least one of the attachment means permits removable attachment of a strap end, thereby enabling one to vary the tension in the strap by modifying the point of attachment along the end of the strap.

The second, or posterior, tension strap permits variable tension control of rearfoot inversion. The posterior tension strap, like the anterior tension strap, has two ends and attachment means provided at each end for attaching the ends to the boot. Both ends of the posterior tension strap are attached to the same side of the proximal segment. The strap extends from its first point of attachment on the proximal segment around the posterior thereof abutting the achilles tendon to the distal segment. The strap continues around the bottom of the distal segment abutting the calcaneus back to its second point of attachment on the same side of the proximal segment.

As with the anterior tension strap, guides may be provided integral with the boot to maintain the position of the posterior tension strap relative to the boot. Also, at least one of the attachment means permits removable attachment of a strap end, thereby enabling one to vary the tension in the strap by modifying the point of attachment along the end of the strap.

Finally, a pair of retention straps are provided which encircle the lower leg and proximal segment to retain the two tension straps as well the proximal flap in their respective positions. The first retention strap is proximally located on the proximal segment above the distally located second retention strap. The first, or proximal, retention strap wraps around the boot at this point to secure the boot on the lower leg. The proximal retention strap also overlaps the adjacent proximal ends of the two tension straps and the proximal flap to further secure them in attachment with the boot.

The second, or distal, retention strap wraps around the boot, but without overlapping the adjacent proximal ends of the tension straps. Instead, the distal retention strap overlaps the posterior tension strap as it extends around the posterior of the proximal segment to retain its desired alignment. An auxiliary strap is, however, provided in conjunction with the distal retention strap which overlaps the adjacent proximal ends of the tension straps and is removably attachable to the distal retention strap to additionally secure attachment of the tension straps to the boot.

An alternate embodiment of the present invention is provided which is substantially identical to the abovedescribed embodiment with the exception of the means by which the boot applies compression to the ankle joint and further with some variations in the configuration of the retention straps. Specifically, the anterior opening is omitted from the alternate embodiment such that the boot is continuous across the anterior. Two parallelly aligned vertical flaps are provided on opposite sides of the boot which have parallel rows of eyelets formed therein. A lace is further provided which is threadable through the eyelets of alternate rows back and forth across the anterior of the boot, thereby providing means for adjustable compression of the boot against the ankle joint when the lace is tightened and tied at its ends.

The alternate embodiment is provided with only a single retention strap that wraps around the proximal segment to secure the boot to the lower leg. This retention strap differs, however, from the previous embodiment in that it simultaneously overlaps the adjacent proximal ends of the anterior and posterior tension straps and the extension of the posterior tension strap around the proximal segment. Thus, a single retention strap secures the adjacent ends of both tension straps in attachment with the boot and retains the posterior tension strap in its desired alignment.

It is apparent from the foregoing description of the ankle brace that particular advantages are realized therewith. As a device for acute rehabilitation, the ankle brace of the present invention is capable of applying adjustable compression and stability to the entire region of the ankle joint even as post-trauma swelling diminishes. Further, the present device can achieve a desirable degree of compression and stability without wearing a shoe in conjunction with the brace.

The present device also offers performance advantages during the return to activity phase of the injury. The brace fits easily within a shoe so that the wearer may engage in mobil activities while wearing the brace. The brace is sufficiently pliant to be comfortable within the shoe, yet sufficiently rigid to provide effective protection and stability to the ankle joint. Finally, as a prophylaxis, the device offers a preferred alternative to conventional taping of the ankle in that it is easy to apply and remove and is tension adjustable even when positioned within a shoe without necessitating removal of the shoe.

The present invention will be further understood, both as to its structure and operation, from the accompanying drawings, taken in conjunction with the accompanying description in which similar reference characters refer to similar parts.

DETAILED DESCRIPTION OF PREFERRED EMBODIMENTS

Figure 1:
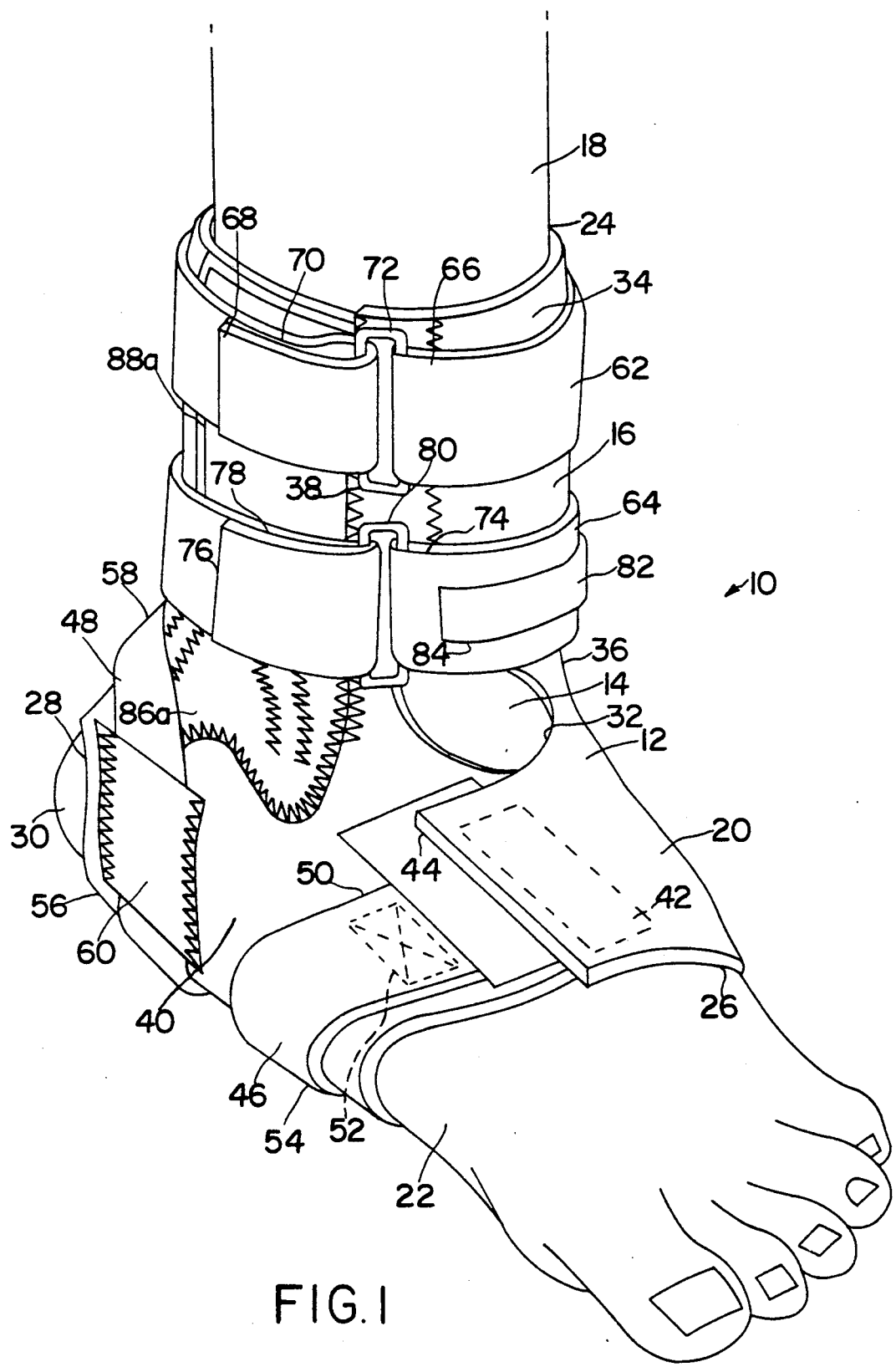
FIG. 1 is a medial perspective view of the ankle brace of the present invention positioned on the ankle of a user.

A first embodiment of the ankle brace of the present invention is described below with reference initially to FIG. 1, wherein a left ankle brace is shown and generally designated 10. It is understood that the foregoing description of a left ankle brace 10 can be adapted to a right ankle brace as well simply by reversing the elements of brace 10 in a manner readily determinable by one skilled in the art from the disclosure provided herein.

Ankle brace 10 comprises a boot 12 substantially enclosing the ankle joint 14. Boot 12 has a proximal segment 16 encircling the lower leg 18 adjacent the ankle joint 14 and a distal segment 20 encircling the foot 22 adjacent the ankle joint 14. Boot 12 is formed from a pliant material that for acute applications is preferably elastic to apply compression to the soft tissue of the ankle joint 14 and the surrounding lower leg 18 and foot 22. A suitable elastic material is a laminate of elasticized nylon fabric and neoprene, such as is well known for use in wetsuits. For prophylactic applications wherein compression is not required, the pliant material of boot 12 may be non-elastic such as a fabric or synthetic leather. Boot 12, as shown in FIG. 1, is preferably formed from a single piece of material that is cut out from a sheet according to a pattern and sewn together at its base to provide it with a tubular configuration.

A proximal opening 24 is provided in proximal segment 16 through which the lower leg 18 enters boot 12. A distal opening 26 is further provided through which foot 22 exits boot 12. Boot 12 also has a posterior opening 28 at the intersection of proximal and distal segments 16 and 20 through which the tuberosity of the calcaneus 30 protrudes to lock the boot 12 in place and prevent migration of the boot 12 along the lower leg 18 or foot 22.

An anterior opening 32 extends the length of boot 12. However, when boot 12 is in place about the ankle joint 14 as shown in FIG. 1, anterior opening 32 is substantially closed except for a small uncovered portion at ankle joint 14. Closure of anterior opening 32 is provided by a proximal flap 34 extending from, and integral with, the lateral face 36 of proximal segment 16. A conventional hook and loop fastener coupling 38, commonly termed VELCRO, is stitched onto the proximal flap 34 and the medial face 40 of proximal segment 16 to enable releasable and adjustable fastening of proximal flap 34 to medial face 40 when flap 34 is pulled across anterior opening 32.

Distal closure of anterior opening 32 is provided by a distal flap 42 extending from, and integral with, the lateral face 36 of distal segment 20. As in the case of proximal flap 34 and proximal segment 16, a conventional hook and loop fastener coupling 44, commonly termed VELCRO, is stitched onto the distal flap 42 and the medial face 40 of distal segment 20 to enable releasable and adjustable fastening of distal flap 42 to medial face 40 when flap 42 is pulled across anterior opening 32.

Ankle brace 10 further comprises a pair of tension straps 46 and 48 formed from a pliant, yet relatively inelastic, material such as an inelastic nylon fabric. The first, or anterior, tension strap 46 is so termed because of its anterior position relative to the second, or posterior, tension strap 48. Anterior tension strap 46 is fixedly attached at its medial end 50 to distal segment 20 by medial stitching 52 and passes under distal segment 20 abutting the plantar vault 54 to releasably connect at its other end not shown with the lateral face 36 of boot 12 in a manner described hereafter.

Posterior tension strap 48 likewise has two ends, but neither are shown in FIG. 1, both being connected to the lateral face 36 of boot 12 in a manner described hereafter. Strap 48 is shown passing under distal segment 20 abutting the calcaneus 56 and passing posteriorly behind distal segment 20 abutting the achilles tendon 58. A medial guide sleeve 60 is integrally provided on distal segment 20 by stitching it thereto, through which strap 48 is slidably retained in a desired orientation relative to the ankle joint 14. Guide sleeve 60 is formed from a pliant, yet relatively inelastic, material such as synthetic leather or inelastic nylon fabric.

Ankle brace 10 is further shown to comprise a pair of retention straps 62 and 64 which may be formed from substantially the same material as tension straps 46, 48. The first, or proximal, retention strap 62 is so termed because of its proximal position relative to the second, or distal, retention strap 64. Proximal retention strap 62 is fixedly attached by stitching at one of its ends 66 to proximal flap 34 and extends around proximal segment 16 abutting the lower leg 18. Strap 62 is releasably and adjustably fastened onto itself at its opposite end 68 by means of a hook and loop fastener coupling 70 after reversing end 68 through rigid loop 72. Proximal retention strap 62 is shown to retain the closure of proximal flap 34 and to apply compression to lower leg 18 across proximal segment 16. Other functions of proximal retention strap 62 are described hereafter.

Distal retention strap 64 is also fixedly attached by stitching at one of its ends 74 to proximal flap 34 and extends around proximal segment 16 abutting the lower leg 18, but below proximal retention strap 62. Strap 64 is releasably and adjustably fastened onto itself at its opposite end 76 by means of a hook and loop fastener coupling 78 after reversing end 76 through rigid loop 80. Distal retention strap 64 is shown to further retain the closure of proximal flap 34 and to apply compression to lower leg 18 across proximal segment 16. Finally, a smaller auxiliary retention strap 82 is positioned on distal retention strap 64 with one end 84 fixedly attached thereto and the other end (not shown) releasably attached which functions in cooperation with distal retention strap 64 as described hereafter.

Further shown in FIG. 1 are a malleolus pocket 86a and a stiffener pocket 88a which are sheaths formed from a pliant inelastic material, such as synthetic leather or inelastic nylon fabric, integrally stitched into the medial face 40 of proximal segment 16. Malleolus pocket 86a retains a retention member and stiffener pocket 88a retains a stiffener member which are described hereafter. Pockets substantially identical to pockets 86a, 88a are provided on the lateral face 36 of proximal segment 16.

Figure 2:
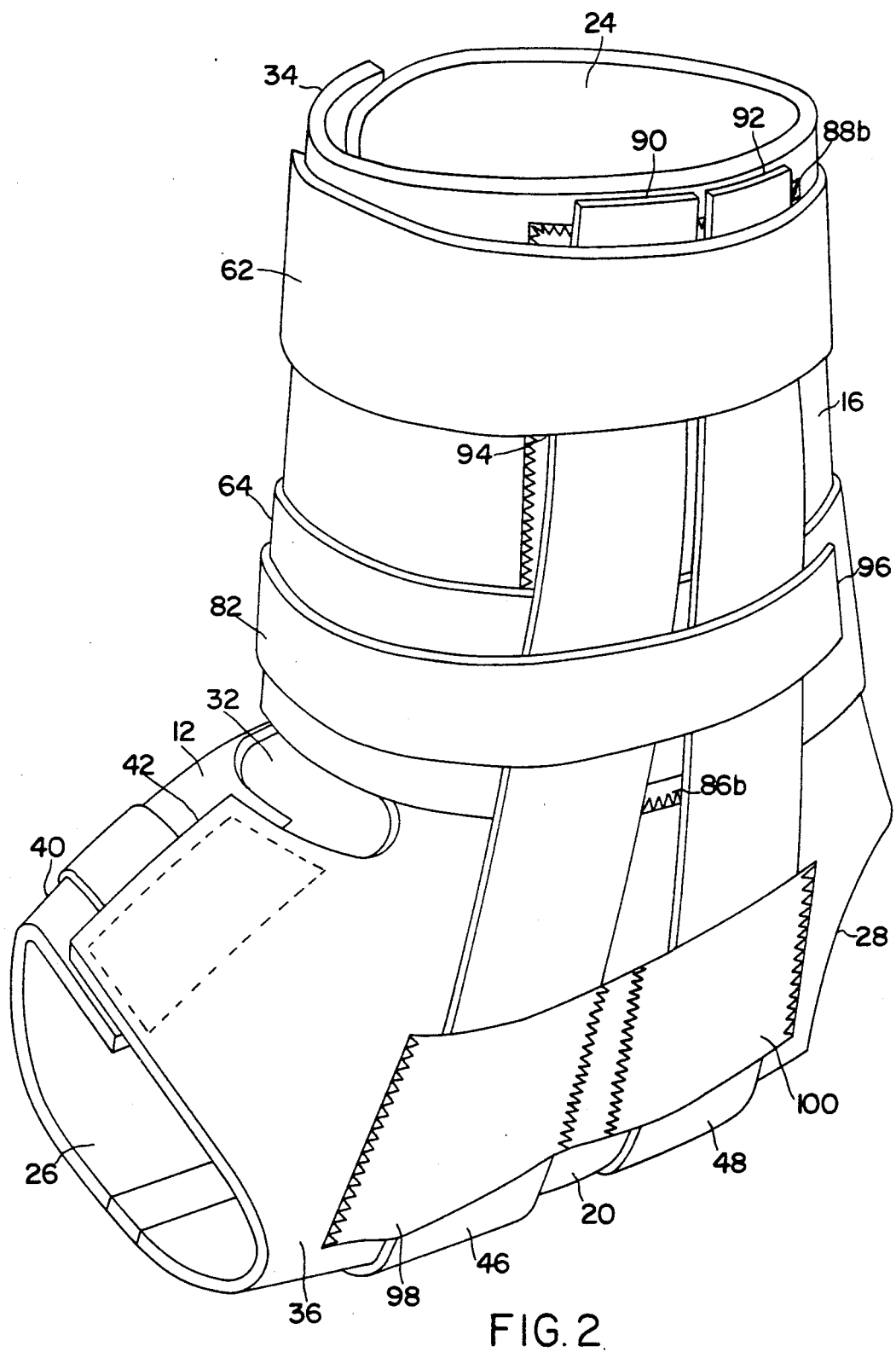
FIG. 2 is a lateral perspective view of the ankle brace as shown in FIG. 1.

Referring now to FIG. 2, the lateral face 36 of brace 10 is shown. Therein it is seen that anterior and posterior tension straps 46, 48 extend from under distal segment 20 and up the lateral face 36 of boot 12. The lateral end 90 of anterior tension strap 46 and a first lateral end 92 of posterior tension strap 48 are releasably and adjustably fastened to the lateral face 36 of proximal segment 16 adjacent to one another by a hook and loop fastener coupling 94 mounted in part on stiffener pocket 88b.

It is noted that proximal retention strap 62 overlaps anterior and posterior tension straps 46, 48, thereby securing the attachment of ends 90, 92 to proximal segment 16, whereas distal retention strap 64 passes underneath tension straps 46, 48. Auxiliary retention strap 82, however, is provided to overlap tension straps 46, 48 and has an end 96 opposite end 84 that is releasably fastened to distal retention strap 64 to further secure straps 46, 48. Finally, lateral guide sleeves 98, 100 similar to medial guide sleeve 60 are provided to slidably retain tension straps 46, 48 in a desired orientation relative to the ankle joint 14.

Figure 3:
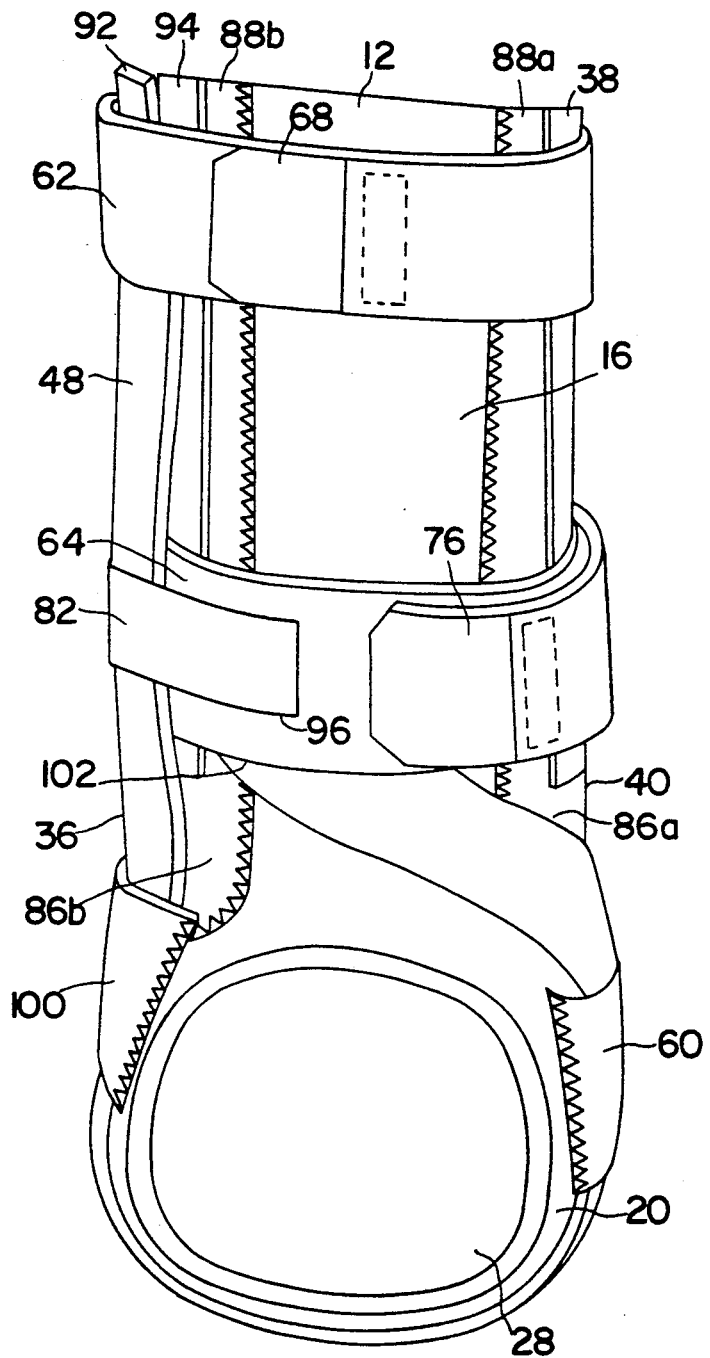
FIG. 3 is an posterior elevational view of the ankle brace as shown in FIG. 1.

The orientation of posterior tension strap 48 and its cooperation with distal retention strap 64 is more clearly seen with reference to FIG. 3. Posterior tension strap 48 has a second lateral end 102 fixably attached to proximal segment 16 beneath distal retention strap 64. As tension strap 48 extends posteriorly across proximal segment 16 in abutment with achilles tendon 58, the overlapping distal retention strap 64 retains strap 48 in a desired orientation relative to the ankle joint 14.

Figure 4:
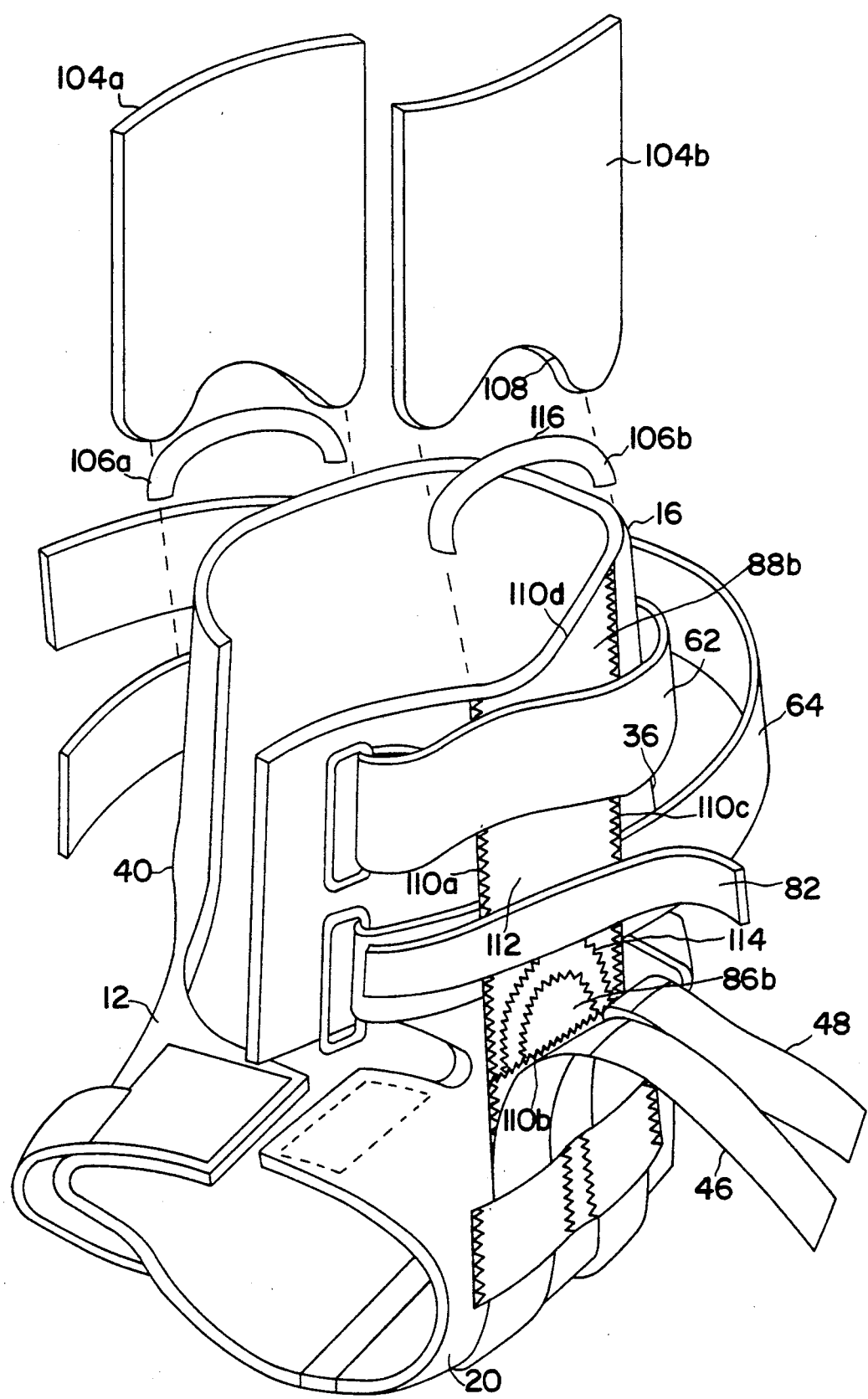
FIG. 4 is an exploded lateral perspective view of the ankle brace of the present invention.

Referring now to FIG. 4, stiffener members 104a, 104b and retention members 106a, 106b are shown outside of malleolus pockets 86a, 86b and stiffener pockets 88a, 88b, respectively. Each stiffener member 104 is a substantially planar sheet of a semi-rigid material, such as a high-strength plastic, which is capable of elastic flex when subjected to sufficient stress. The stiffener member 104 is essentially rectangular except for the distal edge 108 which is curved to conform to the shape of the arcuate retention member 106. Retention member 106 has an arcuate profile and is thicker than stiffener member 104. Retention member 106 is formed from a material which is more pliant than that of the stiffener member 104, yet less pliant than that of the boot 12. A preferred material is felt or a foam.

The stiffener members 104a, 104b and retention members 106a, 106b are incorporated onto the lateral and medial faces 36, 40 of the proximal segment 16 by stitching three sides 110a, 110b, 110c of a patch 112 of appropriate material onto each face, and leaving the proximal side 110d unstitched. The distal side 110b of patch 112 defines the malleolus pocket 86 and the anterior and posterior sides 110a, 110c define the stiffener pocket 88. A retention member 106 is inserted into the malleolus pocket 86 and positioned such that it is downwardly curved to fit around the top edge of the malleolus. Retention member 106 is then sewn into this fixed position by stitches 114. Thereafter, a stiffener member 104 is inserted into the stiffener pocket 88 with the distal edge 108 resting against the crown 116 of the retention member 106. Finally, the proximal edge 110d is stitched shut to retain the stiffener member 104 in the stiffener pocket 88.

With this assembly of boot 12, the stiffener member 104 functions to provide a stable base for the cooperation of straps 46, 48, 62, 64 with boot 12. The retention member 106 functions to prevent the stiffener member 104 from riding too low and rubbing against the malleolus. Accordingly, user discomfort is obviated while wearing the brace 10 and the stiffener members 104a, 104b are retained in their most effective position.

Figure 5:
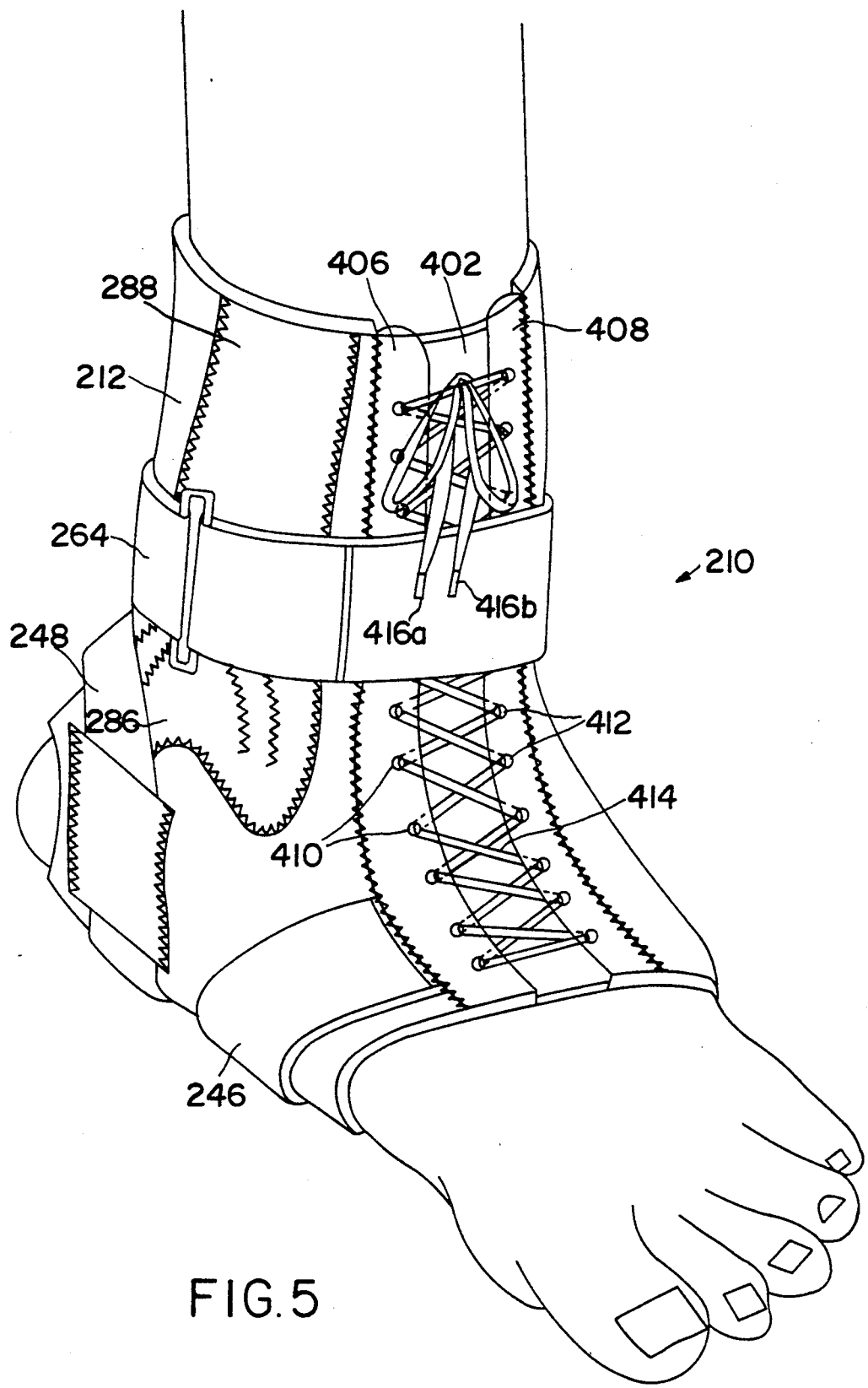
FIG. 5 is a medial perspective view of another embodiment of the ankle brace of the present invention positioned on the ankle of a user.
Figure 6:
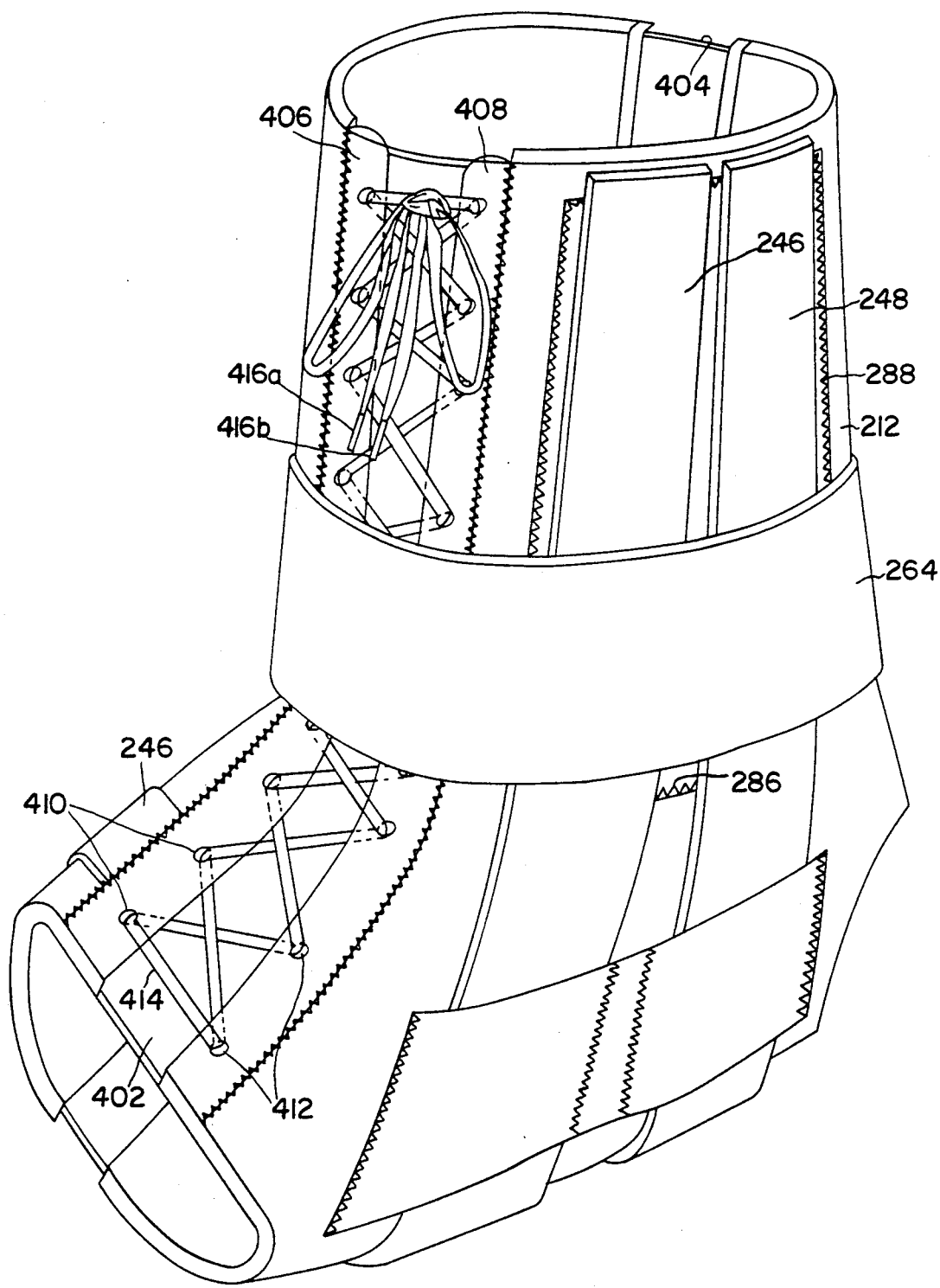
FIG. 6 is a lateral perspective view of the ankle brace as shown in FIG. 5.

An alternate embodiment of the ankle brace of the present invention is described hereafter with reference to FIGS. 5 and 6. The alternate ankle brace is generally designated 210 in FIG. 5. Ankle brace 210 is substantially the same as ankle brace 10 shown in FIGS. 1-4 except that the boot 212 of ankle brace 210 has no anterior opening and, thus, the proximal and distal flaps are omitted from ankle brace 210. To apply compression to the ankle joint 14, the boot 212 is continuous around the ankle joint 14 and anterior and posterior segments 402 and 404 are integrally provided in boot 212.

Anterior and posterior segments 402, 404 are formed from an elastic material such as elasticized nylon fabric. The remainder of boot 212 may likewise be formed from an elastic material or alternatively be formed from a relatively inelastic material, such as synthetic leather or inelastic nylon fabric. Bordering the opposite sides of anterior segment 402 are two parallelly aligned vertical flaps 406, 408 respectively, which have parallel rows of eyelets 410, 412 formed therein. A lace 414 is threaded through alternate rows 410, 412 back and forth across anterior segment 402, thereby providing adjustable compression of boot 212 against the entire ankle joint region when lace 414 is tightened through eyelet rows 410, 412 and tied at lace ends 416a, 416b.

As with the previous embodiment, ankle brace 210 stabilizes the ankle joint 14 by means of anterior and posterior tension straps 246 and 248 shown in FIGS. 5 and 6. Malleolus and stiffener pockets 286, 288 are further provided containing stiffener and retention members (not shown) to cooperate with tension straps 246, 248 for inversion resistance and internal rotation resistance in the same manner as the previous embodiment.

Ankle brace 210 further differs from the previous embodiment in that it has only a single retention strap 264. Retention strap 264 wraps around the boot 212 to secure it to the lower leg 18 while laterally overlapping the anterior and posterior tension straps 246, 248. The retention strap 264 simultaneously posteriorly overlaps the posterior tension strap 248. Thus, retention strap 264 laterally secures both tension straps 246, 248 in attachment with boot 212 and posteriorly retains the posterior tension strap 248 in its desired alignment.

While the particular ankle brace as herein shown and disclosed in detail is fully capable of obtaining the objects and providing the advantages hereinbefore stated, it is to be understood that the brace is merely illustrative of the presently preferred embodiments of the invention and that other embodiments are possible within the scope of the present invention.

I claim:

1. An ankle brace comprising:

a boot defining a posterior, an anterior, and first and second sides, said boot having a proximal segment for encircling the lower leg above the ankle joint and a distal segment for encircling the foot below the ankle joint;

a first tension strap having first and second attachment points positioned thereon separated by a first strap length, said first tension strap attached to said first attachment point to said distal segment on said first side of said boot and said first tension strap attached to said second attachment point to said proximal segment on said second side of said boot, wherein said first or second attachment point is substantially fixedly secured to said boot, and wherein said first strap length is adapted to extend from said first attachment point around the bottom of said distal segment to said second attachment point, thereby enabling adjustment of the tension in said first tension strap; and a second tension strap having third and fourth attachment points positioned thereon separated by a second strap length, said second tension strap attached at said third and fourth attachment points to said proximal segment on said second side of said boot, wherein said third or fourth attachment point is substantially fixedly secured to said boot, and wherein said second strap length is adapted to extend from said third attachment point around said posterior of said proximal segment to said distal segment and around the bottom of said distal segment to said fourth attachment point, thereby enabling adjustment of the tension in said second tension strap.

2. An ankle brace as recited in claim 1 wherein said first tension strap is adapted to extend around the bottom of said distal segment at a point in correspondence with the plantar vault of the foot.

3. An ankle brace as recited in claim 1 wherein said second tension strap is adapted to extend around said posterior of said proximal segment at a point in correspondence with the achilles tendon of the lower leg.

4. An ankle brace as recited in claim 1 wherein said second tension strap is adapted to extend around the bottom of said distal segment at a point in correspondence with the calcaneus of the foot.

5. An ankle brace as recited in claim 1 wherein said first tension strap is adapted to extend around the bottom of said distal segment anterior to where said second tension strap extends around the bottom of said distal segment.

6. An ankle brace as recited in claim 1 wherein said boot is formed from a pliant material.

7. An ankle brace as recited in claim 6 further comprising a pair of first and second stiffening members attached to said first and second sides of said proximal segment respectively, wherein said first and second stiffening members are substantially stiffer than said pliant material.

8. An ankle brace as recited in claim 1 wherein said first attachment point is substantially fixedly secured to said boot.

9. An ankle brace as recited in claim 1 wherein said third attachment point is substantially fixedly secured to said boot.

10. An ankle brace as recited in claim 1 wherein said boot is formed from an elastic material.

11. An ankle brace as recited in claim 1 wherein said boot is formed from an inelastic material.

12. An ankle brace as recited in claim 1 wherein said anterior opening extends across said anterior of said proximal segment and further wherein a first flap is provided to be releasably fastenable to said first or second side of said proximal segment across said anterior opening to adjust the width thereof.

13. An ankle brace as recited in claim 12 wherein said anterior opening extends across said anterior of said distal segment and further wherein a second flap is provided to be releasably fastenable to said first or second side of said distal segment across said anterior opening to adjust the width thereof.

14. An ankle brace as recited in claim 1 further comprising a pair of first and second retention members attached to said first and second sides of said proximal segment respectively wherein said first and second retention members are positioned to conformingly abut the upper portions of the malleoli of the ankle joint.

15. An ankle brace as recited in claim 1 further comprising a retention strap encircling said proximal segment and posteriorly overlapping said second tension strap.

16. An ankle brace as recited in claim 1 further comprising a first row of eyelets and a second row of eyelets formed substantially vertically on opposite sides of said boot respectively, and a lace threadable through said first and second rows of eyelets, thereby providing means for adjusting the tension of said boot around the ankle joint.

17. An ankle brace comprising:
a boot formed from a pliant material defining a posterior, an anterior, and first and second sides, said boot having a proximal segment for encircling the lower leg above the ankle joint and a distal segment for encircling the foot below the ankle joint;
a first tension strap having two ends, wherein a first attachment means is provided for attaching a first end of said first tension strap to said boot and a second attachment means is provided for attaching a second end of said first tension strap to said boot such that said first tension strap is adapted to extend from said first side of said distal segment around the bottom of said distal segment to said second side of said proximal segment, and further wherein at least one of said first and second attachment means provides for releasable attachment of said first tension strap, thereby enabling adjustment of the tension in said first tension strap;
a second tension strap having two ends, wherein a third attachment means is provided for attaching a first end of said second tension strap to said boot and a fourth attachment means is provided for attaching a second end of said second tension strap to said boot such that said second tension strap is adapted to extend from said proximal segment around said posterior of said proximal segment to said distal segment and around the bottom of said distal segment to said proximal segment, and further wherein at least one of said third and fourth attachment means provides for releasable attachment of said second tension strap, thereby enabling adjustment of the tension in said second tension strap;
a pair of first and second stiffening members attached to said first and second sides of said proximal segment respectively, wherein said first and second stiffening members are positioned to conformingly abut the lower leg above the malleoli and are substantially stiffer than said pliant material; and
a pair of first and second retention members attached to said first and second sides of said proximal segment respectively, wherein said first and second retention members are positioned to conformingly abut the upper portions of the malleoli between the malleoli and said stiffening members.

18. An ankle brace comprising:
a boot formed from a pliant material defining a posterior, an anterior, and first and second sides, said boot having a proximal segment for encircling the lower leg above the ankle joint and a distal segment for encircling the foot below the ankle joint;
a first tension strap having two ends, wherein a first attachment means is provided for attaching a first end of said first tension strap to said boot and a second attachment means is provided for attaching a second end of said first tension strap to said boot such that said first tension strap is adapted to extend from said first side of said distal segment around the bottom of said distal segment to said second side of said proximal segment, and further wherein at least one of said first and second attachment means provides for releasable attachment of said first tension strap, thereby enabling adjustment of the tension in said first tension strap;
a second tension strap having two ends, wherein a third attachment means is provided for attaching a first end of said second tension strap to said boot and a fourth attachment means is provided for attaching a second end of said second tension strap to said boot such that said second tension strap is adapted to extend from said proximal segment around said posterior of said proximal segment to said distal segment and around the bottom of said distal segment to said proximal segment, and further wherein at least one of said third and fourth attachment means provides for releasable attachment of said second tension strap, thereby enabling adjustment of the tension in said second tension strap;

a pair of first and second stiffening members attached to said first and second sides of said proximal segment respectively, wherein said first and second stiffening members are positioned to conformingly abut the lower leg above the malleoli and are substantially stiffer than said pliant material;

a pair of first and second retention members attached to said first and second sides of said proximal segment respectively, wherein said first and second retention members are positioned to conformingly abut the upper portions of the malleoli between the malleoli and said stiffening members; and a first row of eyelets and a second row of eyelets formed substantially vertically on opposite sides of said boot respectively, and a lace threadable through said first and second rows of eyelets, thereby providing means for adjusting the tension of said boot around the ankle joint.

* * * * *